United States Patent [19]

Cook et al.

[11] 4,087,506

[45] May 2, 1978

[54] METHOD OF PRODUCING A FLUID ABSORBENT WEB

[75] Inventors: Roy Gordon Cook; James Patrick Jackson, both of Greenwood, S.C.

[73] Assignee: Parke, Davis & Company, Detroit, Mich.

[21] Appl. No.: 711,908

[22] Filed: Aug. 5, 1976

Related U.S. Application Data

[60] Continuation-in-part of Ser. No. 556,243, Mar. 7, 1975, abandoned, which is a division of Ser. No. 402,326, Oct. 1, 1973, Pat. No. 3,888,257.

[51] Int. Cl.² .............................................. D04H 1/20
[52] U.S. Cl. ...................................... 264/112; 264/121
[58] Field of Search ................ 264/109, 121, 113, 112

[56] References Cited

U.S. PATENT DOCUMENTS

| | | | |
|---|---|---|---|
| 2,544,019 | 3/1951 | Heritage | 264/121 |
| 2,981,999 | 5/1961 | Russell | 65/4 R |

Primary Examiner—Robert F. White
Assistant Examiner—James R. Hall
Attorney, Agent, or Firm—David B. Ehrlinger; Stephen Raines; Frank S. Chow

[57] ABSTRACT

A method of producing a fluid absorbent web for the manufacture of disposable absorbent articles is provided, such as diapers, underpads, sanitary napkins or similar articles. The method includes the step of forming a uniform moving web of fiberized wood pulp having a central zone, applying hydrocolloid polymer particles onto the surface of the central zone, and distributing the applied particles into the body of the moving web by air pressure means. Apparatus for producing such articles is also provided featuring means for incorporating absorbent polymer particles within a central zone of a moving web of the matrix.

3 Claims, 8 Drawing Figures

METHOD OF PRODUCING A FLUID ABSORBENT WEB

CROSS-REFERENCE TO RELATED APPLICATION

This application is a Continuation-in-part of copending application Ser. No. 556,243 filed Mar. 7, 1975, now abandoned, which is a Division of Ser. No. 402,326 filed Oct. 1, 1973, now U.S. Pat. No. 3,888,257.

SUMMARY AND DETAILED DESCRIPTION

This invention relates to a method of producing a fluid absorbent web for the manufacture of disposable absorbent articles, such as diapers and the like, more particularly, a method of forming such a web of fiberized wood pulp in which a central zone includes a three-dimensional dispersion of hydrocolloid polymer particles.

Prior art absorbent articles such as diapers, underpads, sanitary napkins, adult incontinent pads and the like have incorporated a cellulose absorbent component for absorption and retention of fluids. Typically, the absorbent components have been sheets of wadding, in particular wadding ranging from about 10 to 25 pounds basis weight per ream. Also used have been layers of the mentioned fiberized wood pulp and in particular layers of a size ranging from about 5 to 25 grams per square foot. In the laboratory these latter components will absorb on a dip and drip-dry basis about 9 to 10 grams of water per gram of wood pulp but at this level of absorbency the wood pulp and in fact the wadding components are squeezable, i.e., when squeezed under pressure free water will run and escape from the material depending upon the amount of pressure applied. Fiberized wood pulp alone is not highly efficient; only a small amount, for example, from 2 to 4 grams of water, is retained per gram of wood pulp. Water absorbent hydrocolloid polymers have been proposed for incorporation with absorbent components of the kind described, but conventional combinations of the same have failed to accommodate flooding or have been expensive or otherwise unsatisfactory.

It is therefore an object of the present invention to provide a method of producing a fluid absorbent web for the manufacture of absorbent products of the kind described.

In accordance with the invention there is provided a method of producing a fluid absorbent web for the manufacture of disposable absorbent articles such as diapers and the like, which includes the steps of forming on a carrier layer such as a wadding layer a dimensionally uniform horizontally moving web of fiberized wood pulp having a body, top and bottom surfaces, and a central zone; applying water absorbent polymer particles onto the top surface across the central zone of the moving web by means of a spreader having a delivery end corresponding in width to the width of the central zone, in the amount of about 1 to 11.5 parts by weight of wood pulp fiber in the central zone for each part by weight of polymer; and distributing the surface applied particles into the moving web by air pressure means such that the particles become mutually dispersed within voids in the body of the central zone of the web, the steps being carried out at a constant rate to produce a web having polymer-free lateral zones and a polymer-containing central zone.

The disposable absorbent article having a matrix made of a length segment of the fluid absorbent web produced by the method of the present invention advantageously maximizes the fluid absorbent properties of both the fiberized wood pulp and the hydrocolloid polymer components, and it does so in a way which makes for a surprisingly high uptake of liquid (to a solid or semi-solid form) and a high absorption capacity, in economical fashion. In this regard, as indicated above, the distribution of hydrocolloid polymer within the absorbent matrix, unlike that of prior art articles, is confined to the central zone (16, FIG. 1 referred to below) of uniform width of the matrix, as viewed in the machine direction leaving the lateral zones (FIG. 1, the parallel zones comprising the lateral edges, outside of the central zone) free of hydrocolloid polymer. It is found that the polymer-free zones of the matrix serve to accomplish quick absorption especially during high loading or flooding conditions and also to hold any liquid overload which under flooding conditions is temporarily beyond the capacity or uptake rate of the polymer-containing central zone. The polymer-free zone of the matrix thereby serves as a standby absorbent until the polymer content of the central zone with passing time has assimilated liquid within the zone at which time the liquid in the outside zones of the matrix begins to migrate inwardly to the central zone where it is irreversibly absorbed by the polymer. For purposes of the invention, the width of the central zone is not critical and may be varied to meet individual requirements. Suitably it can be at least one-third of the width of the matrix, the balance being equally divided between the two lateral free zones. One preferred diaper construction measuring 16 inches × 20 inches has an 8 inch wide central zone, 18 inches in length.

The matrix is further unlike that of the prior art articles in that the hydrocolloid polymer component, instead of being present as a layer or film in laminar relation with a non-polymer absorbent layer, is dispersed uniformly in a three-dimensional configuration within the voids of the matrix so that liquids contacting the matrix exterior (particularly the facing side thereof) are able to penetrate freely within the matrix among the polymer particles, thus having maximum exposure to the surfaces of the polymer particles.

In this regard it has been found that the conventional pulp matrix construction overlaid with a layer of hydrocolloid polymer is poorly absorbent and in fact conducive to undesirable run off under conditions of flooding and in-use pressure. The same matrix according to the invention in which the hydrocolloid polymer is confined within the central zone and well-dispersed within the three dimensions of the matrix provides quite satisfactory results under comparable conditions, with respect to total liquid capacity. The advantages are realized over a wide range of pulp fiber-polymer mixtures. The following description summarizes a demonstration of the effect of varying the weight ratio of pulp fiber to polymer: Using a commercial absorbent starch-acrylonitrile polymer (35-A-100, Grain Processing Corp., Muscatine, Iowa, U.S.A., U.S. Pat. No. 3,661,815) increasing amounts of polymer were mixed with wood pulp fiber to provide a graded series of mixtures and the several mixtures in 6-gram lots were each flooded with water (quantity, 80 cc.). The samples after maximum absorption (30 minutes) were extracted under vacuum similating in-use pressure. Whereas wood fiber pulp alone retains only 2 grams of water under such conditions, the amount of water retained under the conditions of the mentioned test was dramatically increased as follows:

| Absorbent Mixture | Weight of Water Retained Per Gram of Mixture |
| --- | --- |
| 8% polymer/92% pulp | 4.5 gms. |
| 15% polymer/84% pulp | 7.3 gms. |
| 33% polymer/66% pulp | 11.0 gms. |
| 50% polymer/50% pulp | 12.7 gms. |

For purposes of the invention, the polymer may be any physiologically compatible water insoluble hydrocolloid polymer or mixture of such polymers which has, as indicated a water absorbing capacity on a weight basis of at least 50 parts of water per part of polymer. The polymer is used in a form having a relatively high surface to volume ratio such as particles (granules, grains, powder or the like) measuring about 250 microns or less, preferably 90% of which are less than 250 microns and for best results particles of which 90% are less than about 75 microns. A variety of such polymers are commercially available, preferred examples of which are the above-mentioned starch-acrylonitrile polymer and a starch-methacrylonitrile polymer (which U.S. Pat. No. 3,661,815 more particularly discloses are alkali metal carboxylate salts of a starch-polyacrylonitrile graft copolymer and a starch-polymethacrylonitrile graft copolymer, respectively) and polyacrylamide polymer of the type supplied as XD-7343.01 by The Dow Chemical Company, Midland, Michigan, U.S.A., U.S. Pat. No. 3,686,024.

For a better understanding of the invention, reference is made to the annexed drawing in which.

Figure 1:
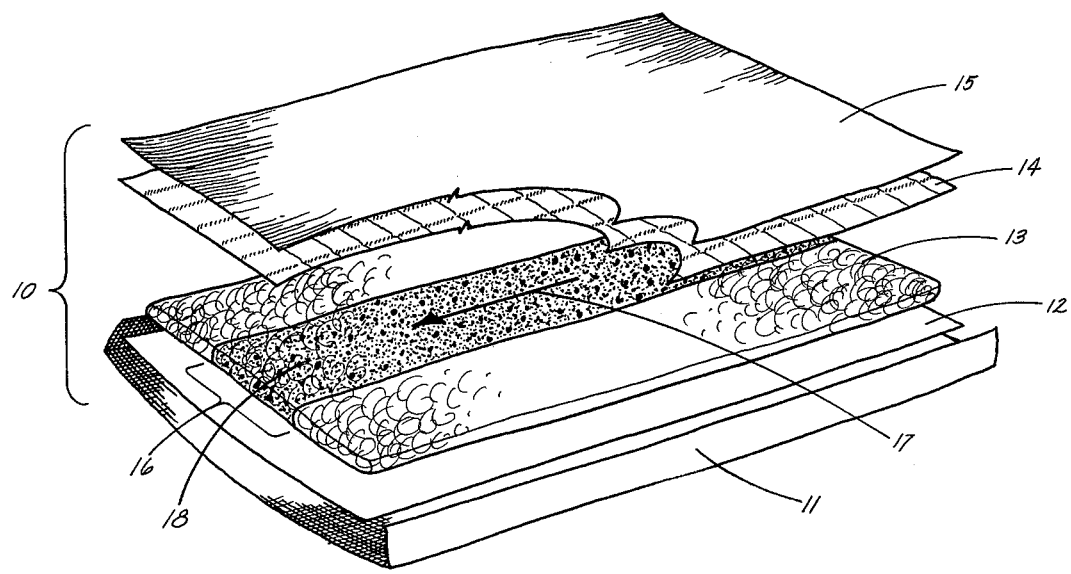
FIG. 1 is a view of a preferred embodiment of a diaper or underpad article.

Referring to FIG. 1, the absorbent diaper or underpad 10 illustrated (which is a preferred embodiment) includes a water-impermeable plastic film backing 11 in layered relation with a wadding sheet or layer 12 and a fiberized wood pulp batt or matrix 13, a second wadding sheet or layer 14, and a non-absorbent liquid permeable facing sheet 15. The central zone 16 of the matrix in line with the machine direction indicated by arrow 17 contains within its voids a three-dimensional dispersion of hydrocolloid polymer particles 18. The mentioned components in the finished article are layered together and held by suitable means such as adhesive in marginal lines or in patterns, pressure bars, and the like to provide a composite blanket-type article which in general outward appearance has a conventional form. In use, body fluid first contacts and passes through the facing 15 to the wadding layer 14 where it is absorbed and redistributed to the matrix 13, usually in the central zone midway thereof in which zone it is absorbed by the polymer particles in a resultant solid or semi-solid form. Under flooding conditions the fluid distributes more widely, particularly to the edges of wadding layer 14 and also to wadding layer 12 and the edges thereof. The backing 11 serves to confine the fluid so that as the absorbent polymer progressively takes up increasing amounts of fluid, the confined fluid in the wadding layers 12 and 14 becomes redistributed toward and into the central zone 16.

Figures 2A, 2B, 2C:
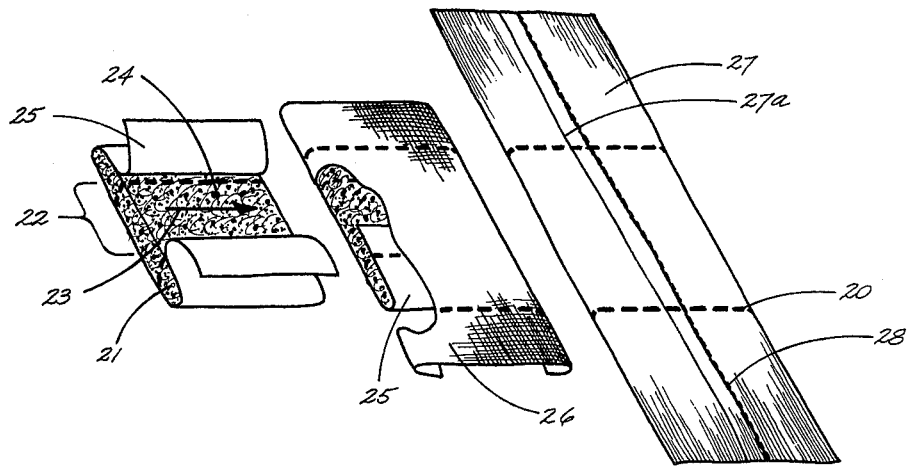
FIGS. 2a, 2b and 2c are views of an absorbent article such as a sanitary napkin in successive stages of manufacture.

FIGS. 2a, 2b and 2c, as indicated, show progressive stages in the production of an absorbent article such as a sanitary napkin 20 having a batt or matrix 21 with a central zone 22 axially aligned with the machine direction (but at right angles to the length of the matrix) indicated by arrow 23. The zone 22 includes a three-dimensional dispersion of hydrocolloid particles 24 and the matrix is covered by an encircling wadding sleeve 25. The covered matrix in turn is partly enclosed or wrapped in a single thickness of water-impervious polymer film 26 and the latter construction is contained in a nonwoven envelope 27 having an edge 27a sealed by suitable means such as an adhesive bead 28.

The component parts of the article can be varied to meet specific requirements. For example, a preferred adult diaper typically measures 16 inches × 20 inches and consists of a 1 mil polyethylene film moisture barrier, a 15 gram per square yard nonwoven rayon cover, a matrix of fiberized bleached wood pulp weighing from about 10 to 20 grams and preferably about 15 grams per square foot, and two layers of 10 pound wadding on both sides of the wood pulp matrix. The matrix in turn has the central zone measuring 8 inches × 18 inches incorporated with a three-dimensional dispersion of hydrocolloid polymer powder in an amount from about 2 to 6 grams. The article containing, for example, hydrocolloid polymer 35-A-100 absorbent starch performs well under flooding conditions. In a performance test comparing the latter diaper with a control diaper lacking the polymer, water in increasing increments was flooded onto the center of the facing of the two diapers. Free water, if any, was then allowed to drip from the diaper while it was held vertical for 10 to 15 minutes, with the following observed result:

| Amount Of Water Applied | Control Diaper Amount Of Water Retained | Polymer Diaper Amount Of Water Retained |
| --- | --- | --- |
| 50 cc. | 37.7 cc. | 50 cc. |
| 100 cc. | 64.4 cc. | 100 cc. |
| 150 cc. | 92.4 cc. | 150 cc. |
| 200 cc. | 117.3 cc. | 200 cc. |
| 250 cc. | 138.5 cc. | 245.1 cc. |
| 300 cc. | 147.6 cc. | 285.4 cc. |
| 350 cc. | 157.1 cc. | 296.8 cc. |

These results show that the polymer diaper was significantly more resistant to run off of water under simulated flooding and pressure conditions. The control diaper immediately lost water at the lowest level of flooding. The same diaper also lost water at all higher water increment levels, whereas the polymer diaper did not lose water until the fifth level of flooding, retaining 245 cc. At that level, by contrast, the control diaper only retained 139 cc.

Figure 3:
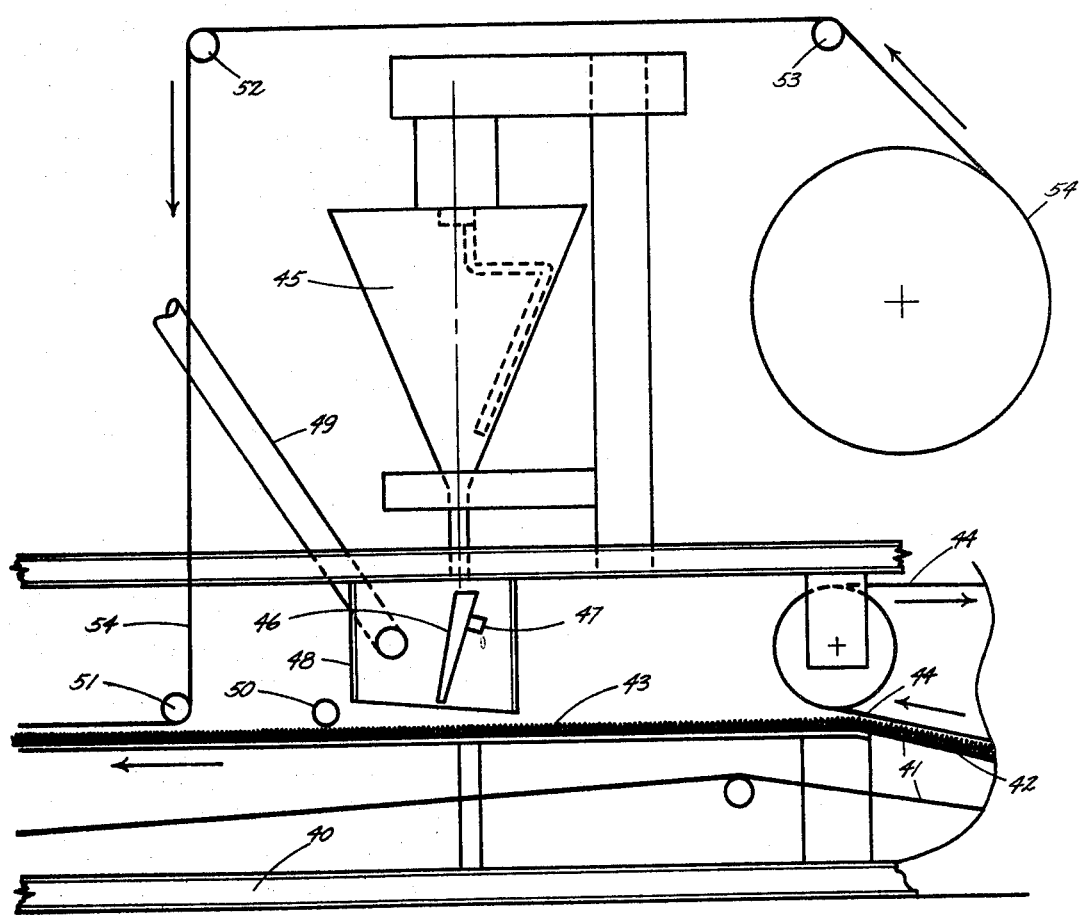
FIG. 3 is a view of a machine for fabricating absorbent articles of the invention.
Figure 4:
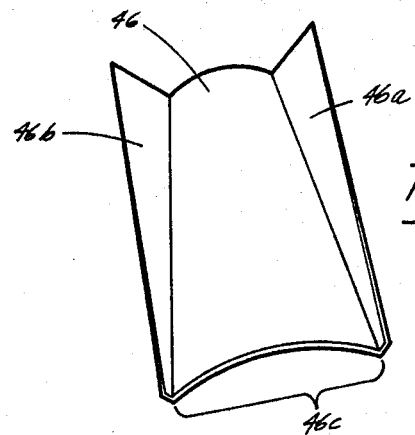
FIG. 4 is a top view of a spreader element of the machine.
Figure 5:
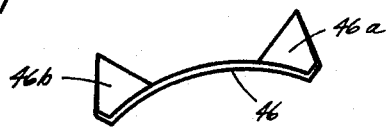
FIG. 5 is an end view of the spreader.
Figure 6:
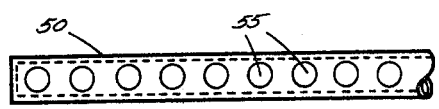
FIG. 6 is a view of the underside of an air manifold component of the machine.

Referring to FIG. 3, one preferred machine embodiment 40 for carrying out the method of the invention has a conveyor surface 41 for conveying an endless layer of wadding 42 on which is formed a fiberized wood pulp mat 43 formed by layering onto a vacuum screen 44. The mat is conveyed at a steady rate below a polymer depositing station which includes a paddle filler or auger filler 45, a spreader 46, and an air vibrator 47 mounted within a dust shroud 48 having an exhaust line 49 for dust removal. The spreader 46, as shown in FIGS. 4 and 5, comprises an arched ramp with side walls 46a and 46b leading to a delivery end 46c of predetermined width corresponding to the width of the central zone 16 of the fluid absorbent web which the machine produces. Downstream of the depositing station is located a compressed air manifold 50 which suitably is a ¼ inch tube sealed at one end projecting laterally across the central zone 16 of the mat 43. Further downstream are reel means 51 for delivering wadding from feeder reels 52 and 53 and a roll of wadding sheet or wadding layer 54. To operate the machine, the same is set up to deliver the wadding layer 42 and wood pulp mat 43 at a constant speed of about 100 feet per minute through the polymer spreader station. The filler 45, charged with polymer particles, is activated with the vibrator 47 to deliver a constant flow of particles from the delivery end of the spreader onto the central zone of the moving wood pulp mat. The air manifold 50 is fed by a low pressure source (not shown, 2 to 3 pounds per square inch) which as seen in FIG. 6 is provided with evenly spaced (about 1 inch apart) orifices 55 located along the bottom of the manifold. The orifices are located just above (about ½ inch) the polymer particles carried by the mat 43 as it moves to the manifold. The air flow from the manifold causes the polymer particles to be extensively dispersed downwardly within the wood fiber mat so that the polymer is well distributed throughout the central zone of the mat instead of lying on top of the central zone of the mat. Other equivalent means for distributing layered polymer particles carried on a mat, such as vacuum means from below the mat (not shown), a combination of pressure above and vacuum (not shown) below the mat, etc., are contemplated by the invention. Finally, the wadding layer 54 moving at the same speed is brought into engagement by reel 51 with the processed mat and carried away for further fabrication as required. Such further fabrication is conventional and does not form a part of the present invention. Thus, for the fabrication of diapers the moving mat is brought into engagement from below with a supporting moisture barrier film backing sheet (fed from a supply reel in the machine direction) and from above with a covering nonwoven moisture pervious facing sheet (also fed from a supply reel in the same direction), thus forming a moving laminated assembly of components of which FIG. 1 illustrates a segment of sufficient length to provide a single diaper. While moving, the laminated web is turned over at the backing edges, cut to diaper length and each diaper sealed by conventional means comprising end seals securing the components in self-sustaining relation.

While the invention has been described in considerable detail, it will be realized by those skilled in the art that wide variation in such detail can be made without departing from the spirit of the invention as claimed below. It is intended that the claims which follow should be interpreted to cover the invention as described and any such variation.

We claim:

1. A method of producing a fluid absorbent web for the manufacture of disposable absorbent articles such as diapers, underpads and sanitary napkins, which includes the steps of forming on a carrier layer a dimensionally uniform horizontally moving web of fiberized wood pulp having a body, top and bottom surfaces, and a central zone; applying water absorbent polymer particles onto the top surface across the central zone of the moving web by means of a spreader having a delivery end corresponding in width to the width of the central zone, in the amount of about 1 to 11.5 parts by weight of wood pulp fiber in the central zone for each part by weight of polymer; and distributing the surface applied particles into the central zone of the moving web by air pressure means such that the particles become mutually dispersed within voids in the body of the central zone of the web, the steps being carried out at a constant rate to produce a web having polymer-free lateral zones and a polymer-containing central zone.

2. Method according to claim 1 where the carrier layer is a layer of wadding.

3. Method according to claim 1 where the polymer particles measure about 250 microns or less.

* * * * *